[19] United States Patent
Kondo et al.
[11] 4,100,184
[45] Jul. 11, 1978

[54] PROCESS FOR PRODUCING 3-CYANOMETHYL CYCLOPENTANONE DERIVATIVES

[75] Inventors: Kiyoshi Kondo, Yamato; Daiei Tunemoto, Sagamihara; Kikuo Sugimoto, Fujino; Yuriko Takahatake, Tokyo, all of Japan

[73] Assignee: Sagami Chemical Research Center, Tokyo, Japan

[21] Appl. No.: 768,908

[22] Filed: Feb. 15, 1977

Related U.S. Application Data

[63] Continuation-in-part of Ser. No. 661,263, Feb. 25, 1976.

[30] Foreign Application Priority Data

Feb. 27, 1976 [JP] Japan ................................ 51-20076

[51] Int. Cl.[2] .................. C07C 120/00; C07C 121/46

[52] U.S. Cl. .................................. 260/464; 252/522; 260/349; 260/593 R; 560/174

[58] Field of Search ........................................ 260/464

[56] References Cited

U.S. PATENT DOCUMENTS 3,954,834 5/1976 Cohen ............................ 260/464 X

*Primary Examiner*—Joseph Paul Brust
*Attorney, Agent, or Firm*—Oblon, Fisher, Spivak, McClelland & Maier

[57] ABSTRACT

A process for producing 3-cyanomethyl cyclopentanone derivatives which are useful precursors of fragrant components in jasmine and analogous thereof such as methyl jasmonoate, methyl dihydrojasmonate, etc., is disclosed. In the process, the jasmonoates are produced starting from β-dicarbonyl compounds and azides through several-step reactions.

6 Claims, No Drawings

PROCESS FOR PRODUCING 3-CYANOMETHYL CYCLOPENTANONE DERIVATIVES

CROSS-REFERENCE TO RELATED APPLICATIONS

This application is a continuation-in-part of application Ser. No. 661,263, filed Feb. 25, 1976.

BACKGROUND OF THE INVENTION

1. Field of the Invention

The present invention relates to a novel process for producing 3-cyanomethyl cyclopentanone derivatives which are useful precursors of fragrant components such as methyl jasmonoate, methyl dihydrojasmonate, etc.

2. Description of the Prior Art

The 3-cyanomethyl cyclopentanone derivatives having the formula

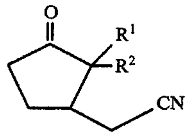
(VI)

wherein $R^1$ represents hydrogen atom or an alkyl group, an alkenyl group or an alkynyl group and $R^2$ represents hydrogen atom, an alkoxycarbonyl group or an acyl group are useful as the precursor of jasmonoides which mean the fragrant components in jasmine and analogous thereof, such as methyl jasmonoate, methyl dihydrojasmonate, etc. which impart the characteristic fragrances of jasmine [E. H. Polak, Cosmetics and Perfumery, 88, 46 (1973)]. These compounds have also been considered to be important as fragrant reinforcing substances.

Various processes for producing jasmonoids have been reported. [T. L. Ho. Syn. Commun., 4, 265 (1974)], for example, the synthesis of methyl jasmonoate from cyclopentanonenamine derivatives [E. Demole, et al., Helv. Chem. Acta, 45, 692 (1962)]; the process for reacting a neucleophilic reagent with a cyclopentanone derivative [G Buchi, et al., J. Org. Chem 36, 2021 (1971); A I Meyers, et al., J Org. Chem. 38, 175 (1973); A. E. Greene, et al., Tetrahedron Lett., 4867 (1976)], the synthesis from indanone derivatives [S. Torii et al., J. Org. Chem. 40, 462 (1975)], the process for using an intermediate obtained by an electrolysis of a norbornane derivative [S. Torii et al., J Org Chem. 40, 2221 (1975)].

These processes respectively have disadvantages that the starting materials are not easily obtained, the selectivity of the reaction is low in some cases, the reaction steps are lengthy, the expensive reagent is needed in some cases, the operation in the reaction is not easy, etc.

The inventors have studied the process for producing jasmonoids in industrial operation and have found the process for easily producing the 3-cyanomethyl cyclopentanone derivative having the formula (VI) which is useful as the precursor of the jasmonoids.

SUMMARY OF THE INVENTION

It is an object of the present invention to provide a process for producing 3-cyanomethyl cyclopentanone derivatives which are useful as the precursor of the jasmonoids by a simple industrial process.

The process of the present invention is summarized by the following reaction scheme:

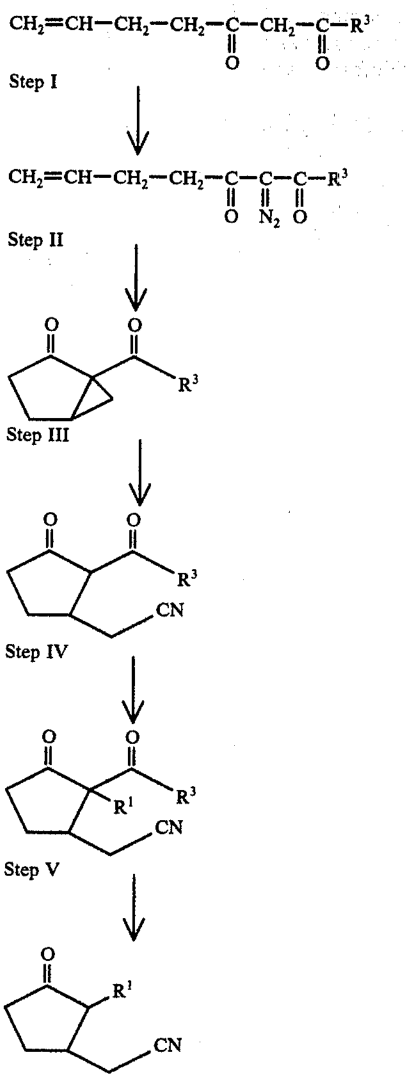

(I)
(II)
(III)
(IV)
(V)
(VI')

wherein $R^1$ represents hydrogen atoms, an alkyl group, an alkenyl group or an alkynyl group and $R^3$ represents an alkoxy group or an alkyl group.

DETAILED DESCRIPTION OF THE EMBODIMENTS

Each step of the synthetic scheme will be illustrated in more detail. It should be noted that the compounds are shown by the typical nomenclature, for example, pentanoic acid ($C_4H_9COOH$) and cyclopentanecarboxylic acid ($C_5H_9COOH$).

In the Step I reaction, the $\beta$-dicarbonyl compounds having the formula

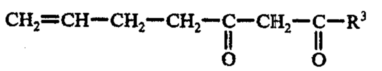
(I)

($R^3$ is defined above) which are the starting material in Step I, can easily be produced by the condensation reaction of acetoacetic acid esters or acetylacetones with alkylhalides (as shown in References).

The typical compounds having the formula (I) include $\beta$-ketoesters such as 3-oxo-6-heptenoic acid esters; and $\beta$-diketones such as 7-octene-2,4-dione and 8-nonene-3,5-dione. The Step I comprises a reaction of the β-dicarbonyl compound (I) with an azide.

The azides can be tosyl azide, benzenesulfonyl azide, phenyl azide, azidoformic acid esters and other various azides.

The reaction of the Step I should be conducted under basic condition. The basic condition can be attained by an addition of alkali metal hydroxides such as sodium hydroxide and potassium hydroxide; alkali metal alkoxides such as sodium methoxide, sodium ethoxide, sodium t-butoxide, potassium t-butoxide; and organic amines such as triethylamine, tributylamine, dimethylaniline, pyridine and piperidine in the reaction system: The necessary amount of the base is preferably about equimole to the starting materials.

In the operation of the Step I, the reaction can be conducted without using a solvent. However in order to increase the yield of the product under mild reaction condition, it is preferable to use a solvent such as acetonitrile, dimethylformamide, tetrahydrofuran, alcohols, ethers, methylene chloride and the like.

When the operation of the Step I is conducted under the said condition, the reaction can smoothly be performed without specific heating or cooling of the system to produce α-diazo-β-dicarbonyl compounds.

The typical α-diazo-β-dicarbonyl compounds having the formula (II)

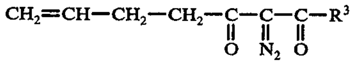

($R^3$ is defined above) which are produced by the operation of the Step (I) include α-diazo-β-ketoesters such as 3-oxo-2-diazo-6-heptenoic acid esters, and α-diazo-β-diketones such as 7-octene-3-diazo-2,4-dione, 8-nonene-4-diazo-3,5-dione and the like.

In the Step II, it is necessary to subject α-diazo-β-dicarbonyl compounds having the formula (II) to the condition which enable the formation of carbene or carbenoid.

The carbene or carbenoid forming condition can be attained by (1) treatment with a catalyst or (2) photoirradiation.

In the catalyzed decomposition method, a trace amount of catalyst such as metals or metal salts e.g. copper powder, copper bronze, copper halides, cupper sulfate, copper acetylacetonate, copper-phosphine complex, silver oxide, silver nitrate and the like, is used in an inert atmosphere to form carbenoids.

In the photodecomposing method, the compound (II) is directly irradiated or irradiated in an inert atmosphere to form carbenes. The conventional light sources used in photochemical industries such as a low pressure mercury lamp as well as high pressure mercury lamp can be used as the light source.

It is not always necessary to use a solvent in either the catalytic method or the photodecomposing method. However, in order to avoid the formation of by-product and to obtain the desired compound in high yield and selectivity, it is preferable to conduct it in an inert medium. The conditions of the inert medium can be attained by conducting the reaction under an inert atmosphere, such as nitrogen or argon gas and using the solvent such as benzene, toluene, xylene, hexane, petroleum ether and the like, as the reaction medium.

The carbenes or carbenoids formed under the said conditions immediately and selectively result in acycloaddition to the unsaturated double bond of the same molecule to produce bicyclo [3.1.0] hexan-2-one derivatives in high yield.

The bicyclo compounds produced by the Step II reaction, have electron withdrawing substituent at 1-position.

Accordingly, it makes easy to cleave the cyclopropane ring by the attack of nucleophile as shown in the next step reaction and the substituent also controls the direction of ring cleavage. In other words, as a result of having this substituent at 1-position, one of the three carbon-carbon bonds of the cyclopropane ring can selectively be cleaved to produce cyclopentanone derivatives.

The typical bicyclo [3.1.0] hexan-2-one derivatives having the formula (III)

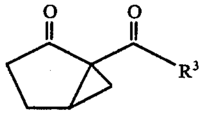

(III)

($R^3$ is defined above) which are produced by the Step II, include 2-oxo-bicyclo [3.1.0] hexane-1-carboxylic acid esters, 1-acetyl-bicyclo [3.1.0] hexan-2-one, 1-propionyl-bicyclo [3.1.0] hexan-2-one and the like.

In the Step III reaction, it is necessary to react the bicyclo [3.1.0] hexan-2-one derivative having the formula (III) with a cyanating reagent in an alkaline condition.

The typical cyanating reagents include hydrogen cyanide, acetone cyanohydrin and metal cyanides such as potassium cyanide, sodium cyanide, copper cyanide, mercury cyanide, aluminum cyanide, etc..

It is necessary to carry out the reaction under basic condition. When an alkali metal cyanide is used, the basic condition can be attained by the addition of the alkali metal cyanide. Accordingly, it is unnecessary to add the other alkaline compound.

When hydrogen cyanide is used, the basic condition can be attained by adding a base such as sodium hydroxide, potassium hydroxide, sodium carbonate, potassium carbonate, triethylamine, pyridine, etc..

It is preferable to carry out the reaction in an inert solvent such as alcohols, ethers and dimethylformamide, N-methylpyrrolidone, acetonitrile, dimethyl sulfoxide, hexamethylphosphoric triamide, etc.

The reaction can be smoothly performed at the room temperature without using a special heating means or a cooling means.

It is considered that the reaction mechanism using a metal cyanide is as follows.

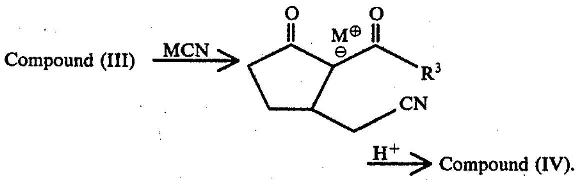

As shown in the reaction formula, a partial ring cleavage of the bicyclo ring of the Compound (III) is carried out by the attack of CN anions of the cyanating reagent to form the anionic active compound and then, the compound is converted to the Compound (IV) by an acid treatment.

In the Step IV reaction, an alkylation is selectively carried out at 1-position of 5-cyanomethyl-2-oxo-cyclopentanecarboxylic acid ester.

The alkylating agents have the formula $R^1Z$ wherein $R^1$ represents an alkyl group, an alkenyl group or an alkynyl group and Z represents a halogen atom, tosyloxy group or acyloxy group.

The reaction is carried out in the presence of a base such as alkali metal carbonates, alkali metal hydroxides, alkali metal alkoxides, alkali metal hydrides, organic amines.

It is preferable to use a solvent such as alcohols, ethers, hydrocarbons, polar solvents e.g. dimethyl sulfoxide, hexamethylphosphoric triamide, etc.

In the Step V reaction, an alkoxycarbonyl group or acyl group at 1-position of 5-cyanomethyl-2-oxo-cyclopentane having the formula (IV) or (V) is eliminated by hydrolyzing it and then heating the hydrolyzed product or by heating it in the presence of an alkali metal salt.

The 3-cyanomethylcyclopentanone having the formula (VI) wherein both $R^1$ and $R^2$ are hydrogen atoms, is obtained from the Compound (IV).

The 3-cyanomethylcyclopentanone derivative having the formula (VI) wherein $R^2$ is hydrogen atom and $R^1$ is the corresponding substituent is obtained from the Compound (V).

These 3-cyanomethylcyclopentanone derivatives having the formula (IV), (V) and (VI) are precursors of jasmonoides.

Preparation 1

A solution of p-toluenesulfonyl azide (592 mg, 3 mmol) in 1 ml of acetonitrile was added at room temperature to a solution of 3-oxo-6-heptenoic acid methyl ester (468 mg, 3mmol) and triethylamine (306 mg, 3 mmol) in 5 ml of acetonitrile.

The mixture was stirred for about 2 hours and the solvent was distilled off under a reduced pressure and the product was dissolved in with 50 ml of ether.

The solution was washed with 5% aqueous solution of potassium hydroxide until no color of the aqueous phase was found and was further washed with a saturated aqueous solution of sodium chloride.

The ether solution was dried over anhydrous magnesium sulfate and was filtered and condensed under a reduced pressure to obtain 530 mg of 2-diazo-3-oxo-6-heptenoic acid methyl ester as yellow oily product. The crude product can be purified by the distillation under a reduced pressure. Yield: 97%. Boiling point: 67 - 68° C/0.4 mmHg. Infrared spectrum ($cm^{-1}$): 2120, 1725, 1655. NMR spectrum ($CCl_4$) $\delta$ : 3.77 (s, 3H), 4.65 - 5.20 (m, 2H), 5.47 - 6.13 (m, 1H).

Preparation 2

In argon atmosphere, the unpurified 2-diazo-3-oxo-6-heptenoic acid methyl ester of Preparation 1 (4.55 g, 25 mmol) was dissolved in 100 ml of benzene.

An anhydrous cupric sulfate (2.5 g) was added as a catalyst to the solution.

The mixture was stirred for about 3 hours under refluxing. After confirming the disappearance of the starting materials by a thin layer chromatography, the reaction mixture was filtered through Celite column.

The solvent was distilled off from the filtrate under a reduced pressure and the remained oily product was distilled under a reduced pressure to obtain 2.92 g of 2-oxo-bicyclo [3.1.0] hexane-1-carboxylic acid methyl ester as oily product. Yield: 69% based on methyl 3-oxo-6-heptenoate. Boiling point: 90° C/0.7 mmHg. NMR spectrum ($CCl_4$) $\delta$ : 1.33 t, J=5Hz, 1H), 1.77 - 2.30 (m, 4H), 2.30 - 2.73 (m, 2H), 3.68 (s, 3H). Mass spectrum(m/e %) : 154 (55), 126 (87), 123 (56), 113 (94), 67 (62), 66 (54), 59 (75). Infrared spectrum ($cm^{-1}$) : 1755, 1725.

Preparation 3

In argon atmosphere, 2-diazo-3-oxo-6-heptenoic acid methyl ester (34 g, 0.187 mmol) was dissolved in benzene (300 ml). An acetyl acetone-copper complex (1 g) was added to the solution. The mixture was stirred for one night under refluxing. After cooling it, the solvent was distilled off under a reduced pressure. The residue was purified by a distillation to obtain 17.1 g of 2-oxo-bicyclo [3.1.0] hexane-1-carboxylic acid methyl ester. Yield: 60%. Boiling point: 83° to 85° C/0.3 mmHg.

Preparation 4

In argon atmosphere, potassium cyanide (290 g, 44 mmol) and 2-oxo-bicyclo [3.1.0] hexane-1-carboxylic acid methyl ester (6.18 g, 40 mmol) was added to dimethyl sulfoxide (15 ml). The mixture was stirred at the room temperature for about three days and was acidified with a diluted hydrochloric acid. The reaction product was extracted with ethyl acetate and dried over anhydrous magnesium sulfate and was concentrated. The residue (7.24 g) was purified by a silica gel column chromatography (ethyl acetate: *n*-hexane=2 : 3) to obtain an oily product.

The product was recrystallized from ethyl acetate and *n*-hexane to obtain 5-cyanomethyl-2-oxo-cyclopentanecarboxylic acid methyl ester (4.7 g). Yield: 65%. Melting point: 49° to 50° C Infrared spectrum ($cm^{-1}$) : 2250, 1755, 1725. NMR spectrum ($CDCl_3$) $\delta$ : 2.10 to 3.35 (m, 8H), 3.80 (s, 3H). Mass spectrum m/e : 181, 141, 109.

Preparation 5

5-Cyanomethyl-2-oxo-cyclopentanecarboxylic acid methyl ester (362 mg, 2 mmol), lithium iodide (350 mg, 2.6 mmol) were dissolved in dimethylformamide (3 ml).

The mixture was heated at 120 C with stirring. After 5 hours, the reaction mixture was cooled and admixed with an aqueous solution of ammonium chloride and the reaction product was extracted wth ethyl acetate. The extract was washed with a saturated sodium chloride aqueous solution and was dried over anhydrous magnesium sulfate and was filtered. The filtrate was concentrated under a reduced pressure. The residue was purified by a silica gel column chromatography (ethyl acetate: *n*-hexane=3 : 7) to obtain 148 mg of 3-cyanomethylcyclopentanone as oily product. Yield: 60%. Infrared spectrum ($cm^{-1}$): 2240, 1740. Mass spectrum m/e : 123, 83, 55, 41.

Preparation 6

In argon atmosphere, sodium cyanide (200 mg, 4 mmol) and 2-oxo-bicyclo [3.1.0] hexane-1-carboxylic acid methyl ester (462 mg, 3 mmol) were added to dimethyl sulfoxide (2ml). The mixture was stirred at the room temperature for one night and was treated in accordance with the process of Preparation 4 to obtain 328 mg of 5-cyanomethyl-2-oxo-cyclopentanecarboxylic acid methyl ester. Yield: 60%.

Preparation 7

In argon atmosphere, potassium cyanide (260 mg, 4 mmol) and 2-oxo-bicyclo [3.1.0] hexane-1-carboxylic acid methyl ester (462 mg, 3 mmol) were added to hexamethylphosphoric triamide (3 ml). The mixture was stirred at the room temperature for 24 hours and was treated in accordance with the process of Preparation 4 to obtain 300 mg of 5-cyanomethyl-2-oxo-cyclopentanecarboxylic acid methyl ester. Yield: 55%.

Preparation 8

In argon atmosphere, potassium cyanide (260 mg, 4 mmol) and 2-oxo-bicyclo [3.1.0] hexane-1-carboxylic acid methyl ester (462 mg, 3 mmol) were added to dimethylformamide (3 ml). The mixture was stirred at the room temperature for 24 hours and was treated in accordance with the process of Preparation 4 to obtain 290 mg of 5-cyanomethyl-2-oxo-cyclopentanecarboxylic acid methyl ester. Yield: 53%.

Preparation 9

3-Cyanomethyl-2-oxo-cyclopentanecarboxylic acid methyl ester (4.17 g, 23 mmol) and 1-bromo-2-pentyne (4.06 g, 27.5 mmol) were dissolved in acetone (40 ml).

Potassium carbonate (3.19 g, 23 mmol) was added to the solution. The mixture was heated under refluxing with vigorously stirring for one night. After cooling the reaction mixture, the solvent was distilled off under a reduced pressure.

The residue was admixed with water and the reaction product was extracted with ethyl acetate and was dried over anhydrous magnesium sulfate and then the solvent was distilled off under a reduced pressure.

The residue was recrystallized from ethyl acetate and *n*-hexane to obtain 2.77 g of 5-cyanomethyl-2-oxo-1-(2'-pentynyl)-cyclopentanecarboxylic acid methyl ester as white crystals. Yield: 49%. Melting point: 100 to 101° C. Infrared spectrum ($cm^{-1}$) : 2250, 1753, 1730. NMR spectrum ($DCCl_3$) δ : 1.08 (t, J=6.5Hz, 3H), 1.90 - 3.09 (m, 11H), 3.67(s, 3H). Mass spectrum(m/e) : 247, 216, 188.

Preparation 10

5-Cyanomethyl-2-oxo-cyclopentanecarboxylic acid methyl ester (543 mg, 3 mmol) and 1-bromo-2-pentyne (485 mg, 3.3 mmol) were dissolved in acetone (15 ml). Potassium carbonate (415 mg, 3 mmol) was added to the solution. The mixture was heated under refluxing with vigorously stirring for one night. After cooling the reaction mixture, the solvent was distilled off under a reduced pressure. The residue was directly purified by a silica gel column chromatography (ethyl acetate: *n*-hexane=1 : 4) to obtain 630 mg of 5-cyanomethyl-2-oxo-1-(2'-pentynyl)-cyclopentanecarboxylic acid methyl ester as white crystals. Yield: 85%

Preparation 11

5-Cyanomethyl-2-oxo-1-(2'-pentynyl)-cyclopentane carboxylic acid methyl ester (4.94 g, 20 mmol) was dissolved in dimethyl sulfoxide (10 ml). Lithium iodide (5.36 g, 40 mmol) was added to the solution with stirring and the mixture was stirred at 130° C for 3 hours and was cooled to the room temperature.

The reaction mixture was purified by a silica gel column chromatography (ethyl acetate: *n*-hexane=3 : 7) to obtain 3.2 g of 3-cyanomethyl-2-(2'-pentynyl)-cyclopentanone as oily product. Yield: 85%.

Preparation 12

3-Cyanomethyl-2-(2'-pentynyl)-cyclopentanone (378 mg, 2 mmol) was dissolved in anhydrous methanol (10 ml). Lindlar catalyst (240 mg) was added to the solution. Hydrogen (49 ml) was fed into the mixture. After hydrogen addition, the reaction mixture was concentrated and the residue was purified by a silica gel column chromatography (ethyl acetate: *n*-hexane=1 : 4) to obtain 3-cyanomethyl-2-(cis-2'-pentenyl)-cyclopentanone (275 mg) as oily product. Yield: 72%. Infrared spectrum ($cm^{-1}$) : 2248, 1745. NMR spectrum ($CDCl_3$) δ : 0.97 (t, J=7Hz, 3H), 1.52 - 3.00 (m, 12H), 4.95 - 5.80 (m, 2H).

Preparation 13

3-Cyanomethyl-2-(2'-pentynyl)-cyclopentanone (2.49 g, 13.2 mmol) was dissolved in anhydrous methanol (25 ml). Freshly prepared Lindlar catalyst (750 mg) was added to the solution. Hydrogen (323 ml) was fed over the mixture. After the check of the completion of the equimolar hydrogen absorption by gas chromatography, the reaction mixture was filtered through Celite layer. The filtrate was concentrated under a reduced pressure and the residue was distilled to obtain 2.28 g of 3-cyanomethyl-2-(cis-2'-pentenyl)-cyclopentanone.
Yield: 90% Boiling point: 126°–130° C/1.0 mmHg Preparation 14

5-Cyanomethyl-2-oxo-cyclopentanecarboxylic acid methyl ester (100 mg, 0.58 mmol) and allyl bromide (121 mg, 1 mmol) were dissolved in acetone (5ml). Potassium carbonate (138 mg, 1 mmol) was added to the solution. The mixture was heated under refluxing with stirring for 5 hours and then was cooled and was filtered. The filtrate was concentrated under a reduced pressure. The residue was purified by a silica gel column chromatography (ethyl acetate: *n*-hexane=1: 4) to obtain 89 mg of 1-allyl-5-cyanomethyl-2-oxo-cyclopentanecarboxylic acid methyl ester as viscous oily product. Yield: 69%. Infrared spectrum($cm^{-1}$): 2235, 1755, 1730, 1640, 925. NMR spectrum ($CDCl_3$) δ : 1.60 - 3.05 (m, 9H), 3.73 (s, 3H), 4.88 - 6.07 (m, 3H).

Preparation 15

1-Allyl-5-cyanomethyl-2-oxo-cyclopentanecarboxylic acid methyl ester (220 mg, 1 mmol) and lithium iodide (2.68 mg, 2 mmol) were dissolved in dimethylformamide (3 ml).

The solution was stirred at 120° C for 5 hours and was cooled and was admixed with an aqueous solution of ammonium chloride. The reaction product was extracted with ethyl acetate and the extract was washed with a saturated sodium chloride aqueous solution and was dried over anhydrous magnesium sulfate, and was filtered. The filtrate was concentrated under a reduced pressure and the residue was purified by a silica gel column chromatography (ethyl acetate : *n*-hexane=1 : 4) to obtain 90 mg of 2-allyl-3-cyanomethyl-cyclopentanone as oily product. Yield: 55%. Infrared spectrum ($cm^{-1}$) : 2240, 1740, 1640, 920. NMR spectrum ($CDCl_3$) δ : 1.60 - 3.05 (m, 10H), 4.83 - 6.07 (m, 2H).

Preparation 16

3-Cyanomethyl-2-(cis-2'-pentenyl)-cyclopentanone (220 mg, 1.15 mmol) was dissolved in a mixture of ether (20 ml) and methanol (5 ml). The solution was cooled to 0° C and dry hydrogen chloride gas was fed into the solution to saturate it and the solution was kept for one night.

Argon gas was passed through the solution to remove excess hydrogen chloride. The reaction mixture was poured on 50 g of ice and was stirred for 30 minutes. Sodium chloride was added to the water phase and the reaction product was extracted with ethyl acetate. The extract was washed with a saturated sodium chloride aqueous solution and then, was dried over anhydrous magnesium sulfate and was filtrated. The solvent was distilled off under a reduced pressure and the residue was purified by a silica gel column chromatography (ethyl acetate: *n*-hexane=1 : 9) to obtain 188 mg of 3-methoxycarbonylmethyl-2-(cis-2'-pentenyl)-cyclopentanone.(methyl jasmonate). Yield: 73%. Infrared spectrum ($cm^{-1}$) : 1740, 1160. NMR spectrum ($CDCl_3$) δ : 0.94 (t, J=7Hz, 3H), 1.40 - 2.90 (m, 12H), 3.64 (s, 3H), 5.30 (m, 2H).

Preparation 17

3-Cyanomethyl-2-(cis-2'-pentenyl)-cyclopentanone (4.0g, 21 mmol) was dissolved in a mixture of ether (80 ml) and methanol (50 ml). The solution was cooled to 0° C and dried hydrogen chloride gas was fed into the solution to saturate it. The reaction mixture was allowed to stand in refrigerator for one night. Argon gas was passed through the solution to remove excess hydrogen chloride. Then the reaction mixture was concentrated under a reduced pressure to remove the almost solvent used. The mixture of ether, ice and water was added to the residue. The reaction mixture was stirred over night. Sodium chloride was added to the water phase and the reaction product was extracted with ether and several times with ethyl acetate. The aqueous layer was neutralized with cold 10% aqueous sodium hydroxide and extracted with ethyl acetate. The combined organic layer was washed with brine and was dried over anhydrous magnesium sulfate and was filtered. The solvent was distilled off under a reduced pressure and the residue was purified by a silica gel column chromatography (ethyl acetate : *n*-hexane=1.5 : 8.5) to obtain 3.96 g of 3-methoxycarbonylmethyl-2-(cis-2'-pentenyl)-cyclopentanone. (methyl jasmonate). Yield: 84%. Preparation 18:

In argon atmosphere, sodium cyanide (2.16 g, 44 mmol) and 2-oxo-bicyclo[3.1.0]hexane-1-carboxylic acid methyl ester (6.18 g, 40 mmol) were added to dimethyl sulfoxide (40 ml). The mixture was stirred at room temperature for 24 hours and was acidified with a diluted hydrochloric acid. The reaction product was extracted several times with ethyl acetate. The combined ethyl acetate layer was washed with brine and dried over anhydrous magnesium sulfate and was concentrated to give oily residue (7.79 g) which was mainly composed of 5-cyanomethyl-2-oxo-cyclopentane carboxylic acid methyl ester. The oily residue obtained above and 1-bromo-2-pentyne (6.32 g, 43 mmol) were dissolved in acetone (70 ml). Potassium carbonate (5.94 g, 43 mmol) was added to the solution. The mixture was heated under refluxing with vigorously stirring overnight. After cooling the reaction mixture, it was filtered through Celite layer and the filtrate was concentrated under a reduced pressure to give the semi-solid residue (10.32 g) which was mainly composed of 5-cyanomethyl-2-oxo-1-(2'-pentynyl)cyclopentane carboxylic acid methyl ester.

Then, the semi-solid residue obtained above was dissolved in dimethyl sulfoxide (20 ml). Lithium iodide (5.36 g, 40 mmol) was added to the solution with stirring and the mixture was stirred at 130° C for 3 hours and was cooled to the room temperature. The reaction mixture was neutralized with aqueous ammonium chloride solution and extracted several times with ethyl acetate. The combined organic layer was washed with brine and dried over anhydrous magnesium sulfate and was filtered. The filtrate was concentrated under a reduced pressure to obtain the oily residue. The residue was purified by distillation to obtain 2.48 g of 3-cyanomethyl-2-(2'-pentynyl)-cyclopentanone as an oil. Yield: 33% [overall yield based on 2-oxo-bicyclo[3.1.0]-hexane-1-carboxylic acid methyl ester] Boiling point: 135°-142° C/0.9 mmHg Reference 1

In accordance with the process of Preparation 1, 7-octene-2,4-dione (8.4 g; 60 mmol), triethylamine (6.1g; 60 mmol) and p-toluenesulfonyl azide (11.8 g; 60 mmol) were used as starting materials and the final product was purified by silica gel column chromatography with a mixture of ethylacetate: *n*-hexane=1:9, to obtain 8.4 g of 7-octene-3-diazo-2,4-dione as a yellow oily product. Yield: 84%. Infrared spectrum ($cm^{-1}$); 2115, 1665; NMR spectrum ($CCl_4$), δ; 2.10 - 2.50 (m, 2H), 2.30 (s, 3H), 2.50 - 2.90 (m, 2H), 4.63 - 5.20 (m, 2H), 5.37 - 6.16 (m, 1H).

Reference 2

In accordance with the process of Preparation 2, the 7-octene-3-diazo-2,4-dione of Reference 1 (8.17 g; 49 mmol) and anhydrous cupric sulfate (5 g) were used to obtain 2.52 of 1-acetyl-2-oxo-bicyclo [3.1.0] hexane as an oily product. Yield: 37%. Boiling point: 55° - 57° C/0.15 mmHg;

Infrared spectrum ($cm^{-1}$); 1725, 1690; NMR spectrum ($CCl_4$)δ: 1.37 (dd, J = 4 Hz, J = 6 Hz, 1H), 1.76 - 2.70 (m, 6H), 2.40 (s, 3H).

What is claimed is:

1. A method for producing a fragrant 3-cyanomethyl-cyclopentanone jasmonoide intermediate having the formula:

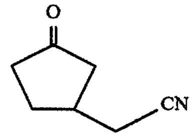

which comprises:

reacting a bicyclo[3,1,0] hexane derivative having the formula:

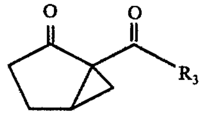

wherein $R^3$ represents alkoxy or alkyl, with a cyanating agent selected from the group consisting of hydrogen cyanide, acetone cyanohydrin and metal cyanides under basic conditions in an inert solvent; and eliminating said

group when said $R^3$ is alkoxy, by first hydrolyzing said cyanated hexane derivative and then decarboxylating said hydrolyzed hexane derivative or by heating said cyanated hexane derivative in the presence of an alkali metal salt when said $R^3$ group is alkyl.

2. A method for producing a fragrant 3-cyanomethylcyclopentanone jasmonoide intermediate having the formula:

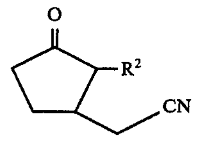

wherein $R^2$ represents alkoxycarbonyl or acyl, which comprises:

reacting a bicyclo [3,1,0] hexane derivative having the formula:

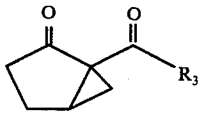

wherein $R^3$ represents alkoxy or alkyl, with a cyanating agent selected from the group consisting of hydrogen cyanide, acetone cyanohydrin and metal cyanides under basic conditions in an inert solvent.

3. A method for producing a fragrant 3-cyanomethylcyclopentanone jasmonoide intermediate having the formula:

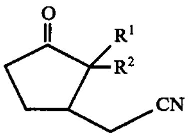

wherein $R^1$ represents alkyl, alkenyl or alkynyl and $R^2$ represents alkoxycarbonyl or acyl, which comprises:

reacting a bicyclo [3,1,0] hexane derivative having the formula:

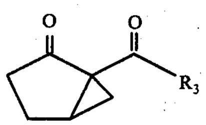

wherein $R^3$ represents alkoxy or alkyl, with a cyanating agent selected from the group consisting of hydrogen cyanide, acetone cyanohydrin and metal cyanides under basic conditions in an inert solvent; and alkylating said cyanated hexane derivative with an alkylating agent of the formula $R^1Z$, wherein $R^1$ is alkyl, alkenyl or alkynyl and Z is halogen, or acyloxy under basic conditions in a solvent.

4. A method for producing a fragrant 3-cyanomethylcyclopentanone jasmonoide intermediate having the formula:

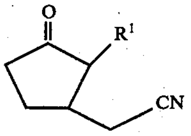

wherein R' represents alkyl, alkenyl, or alkynyl, which comprises:

reacting a bicyclo[3,1,0] hexane derivative having the formula:

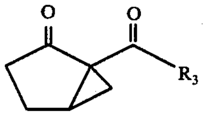

wherein $R^3$ represents alkoxy or alkyl, with a cyanating agent selected from the group consisting of hydrogen cyanide, acetone cyanohydrin and metal cyanides under basic conditions in an inert solvent;

alkylating said cyanated hexane derivative with an alkylating agent of the formula $R^1Z$, wherein $R^1$ is alkyl, alkenyl or alkynyl and Z is halogen, or acyloxy under basic conditions in a solvent; and eliminating said

group when said $R^3$ is alkoxy, by first hydrolyzing said cyanated hexane derivative and then decarboxylating said hydrolyzed hexane derivative or by heating said cyanated hexane derivative in the presence of an alkali metal salt when said $R^3$ group is alkyl.

5. The method of claim 3, wherein said acyloxy group of group Z is tosyloxy.

6. The method of claim 4, wherein said acyloxy group of group Z is tosyloxy.

* * * * *